US008313748B2

(12) United States Patent
Lindahl

(10) Patent No.: US 8,313,748 B2
(45) Date of Patent: Nov. 20, 2012

(54) FUSION PROTEIN VACCINE

(75) Inventor: Gunnar Lindahl, Lund (SE)

(73) Assignee: Minervax Aps, Kongens Lyngby (DK)

( * ) Notice: Subject to any disclaimer, the term of this patent is extended or adjusted under 35 U.S.C. 154(b) by 372 days.

(21) Appl. No.: 12/596,249

(22) PCT Filed: Apr. 14, 2008

(86) PCT No.: PCT/SE2008/000270
§ 371 (c)(1),
(2), (4) Date: Oct. 16, 2009

(87) PCT Pub. No.: WO2008/127179
PCT Pub. Date: Oct. 23, 2008

(65) Prior Publication Data
US 2010/0062015 A1 Mar. 11, 2010

Related U.S. Application Data

(60) Provisional application No. 60/940,473, filed on May 29, 2007.

(30) Foreign Application Priority Data

Apr. 16, 2007 (SE) .................................. 0700919-4

(51) Int. Cl.
*A61K 39/00* (2006.01)
*A61K 39/02* (2006.01)
*A61K 39/09* (2006.01)
*A61K 39/385* (2006.01)
*C07K 1/00* (2006.01)

(52) U.S. Cl. ............. 424/185.1; 424/197.11; 424/234.1; 424/244.1; 530/350

(58) Field of Classification Search ........................ None
See application file for complete search history.

(56) References Cited

U.S. PATENT DOCUMENTS

| 4,225,579 A | * | 9/1980 | Kleinberg | ........................ 424/48 |
| 4,496,538 A | | 1/1985 | Gordon | |
| 4,879,213 A | * | 11/1989 | Fox et al. | ........................... 435/5 |
| 6,063,386 A | | 5/2000 | Dale et al. | |
| 6,855,321 B1 | | 2/2005 | Rappuoli et al. | |

FOREIGN PATENT DOCUMENTS

| EP | 0 866 133 | 9/1998 |
| WO | WO 94/01031 | 1/1994 |
| WO | WO 94/10317 | 5/1994 |
| WO | WO 94/21685 | 9/1994 |
| WO | WO 2005/028618 | 3/2005 |

OTHER PUBLICATIONS

Plotkin et al (Vaccines WB Saunders Company, 1988, p. 571).*
Brimil et al. "Epidemiology of *Streptococus agalactiae* colonization in Germany." *Int. J. of Med. Microbiol.* vol. 296. 2006. pp. 39-44.
Creti et al. "Multiplex PCR Assay for Direct Identification of Group B Streptococcal Alpha-Protein—Like Protein Genes." *J. of Clin. Microbiol.* vol. 42. No. 3. 2004. pp. 1326-1329.
Gravekamp et al, "Immunogenicity and Protective Efficacy of the Alpha C Protein Group B Streptococci Are Inversely Related to the Number of Repeats." *Infectioni and Immunity.* vol. 65. No. 12. 1997. pp. 5216-5221.
Larsson et al. "Protection against experimental infection with group B *Streptococcus* by immunization with a bivalent protein vaccine," *Vaccine* vol. 17, 1999, pp. 454-458.
Liljeqvist et al, "Production of recombinant subunit vaccines: protein immunogens, live delivery systems and nucleic acid vaccines." *J. of Biotech.* vol. 73. 1999. pp. 1-33.
Lindahl et al. "Surface Proteins of *Streptococcus agalacitae* and Related Proteins in Other Bacterial Pathogens." *Clin. Microbiol. Rev.* vol. 1. 2005. pp. 102-127.
Maoine at al. "Identification of a Universal Group B *Streptococcus* Vaccine by Multiple Genome Screen." *Science.* vol. 309. 2005. pp. 148-150.
Needleman et al. "A General Method Applicable to the Search for Similarities in the Amino Acid Sequence of Two Proteins." *J. Mol. Biol.* vol. 48. 1970. pp. 443-453.
Perez-Casal et al, "An M protein with a single C repeat prevents phagocytosis of *Steptococcus pyogene*:use of a temperature-sensitive shuffle vector to deliver homologous sequences to the chromosome of *S. pyogenes.*" *Molecular Microbiol.* vol. 8. No. 5. 1993, pp. 809-819.
Pritchard et al. "Murine Monoclonal Antibodies to Type Ib Polysaccharide of Group B Streptococci Bind to Human Milk Oligosaccharides." *Infection & Immunity.* vol. 60. No. 4. 1992. pp. 1598-1602.
Schneerson et al. "Quantitative and Qualitative analyses of Serum Antibodies Elicited in Adults by *Haemophilus influenzae* Type b and pneumococcus Type 6A Capsular Polysaccharide—Tetnus Toxoid Conjugates." *Infection and Immunity.* vol. 52. No. 2. 1986. pp. 519-528.
Seid et al. "Preparation and Characterization of Detoxified Lipopolysaccharide-Protein Conjugates." *J. of Biol. Chem.* vol. 296. No. 14. 1981. pp. 7305-7310.
Smith et al. "Comparison of Biosequences." *Adv. in Applied Math.* vol. 2. 1981. pp. 482-489.
Stalhammar-Carlemalm et al, "Nonimmuunodominant Regions are effective as Building Blocks in Streptococcal Fusion Protein Vaccine." *Cell Host & Microbe.* vol. 2. 2007. pp. 427-434.
Stalhammar-Carlemalm et al. "The R28 protein of *Streptococcus pyogenes* is related to several group B streptococcal suface proteins, confers protective immunity and promotes binding to human epithelial cells." *Molecular Micro.*vol. 33. No. 1. 1999. pp. 208-219.
Szu et al. "Ultrasonic irradiation of bacterial polysaccharides." *Carbohydrate Research.* vol. 152. 1986. pp. 7-20.

(Continued)

*Primary Examiner* — Albert Navarro
(74) *Attorney, Agent, or Firm* — Merchant & Gould P.C.

(57) ABSTRACT

The present invention relates to the fields of microbiology and vaccine technology, and concerns the development of a vaccine capable of conferring immunity to group B *Streptococcus* infections. More particularly, the present invention relates to a novel fusion protein, comprising N-terminal region fragments of group B *Streptococcus* surface proteins, which confers immunity to invasive strains of the group B *Streptococcus*. It further pertains to an isolated nucleotide sequence encoding said fusion protein; a vector; a host cell; a vaccine; and a method for preventing or treating a group B *Streptococcus* infection.

11 Claims, 5 Drawing Sheets

OTHER PUBLICATIONS

Waldermarsson et al. "The Streptococall Blr and Slr Proteins Define a Family of Surface Proteins with Leucine-Rich Repeats. Camouflaging by Other surface structures." *J. of Bacteriology*. vol. 188. No. 2. 2006. pp. 378-388.

Wastfelt et al. "Identification of a Family of Streptococcal Surface Proteins with Extremely Repetitive Structure." *J. of Biological Chem*. vol. 271. No. 31. 1996. pp. 18892-18897.

Larsson et al. "Assocation between low concentrations of antibodies to protein α and Rib and invasive neonatal group B streptococcal infection," *Arch Dis. Child. Fetal Neonatal Ed*. vol. 91. 2006.

Russian Office Action for Russian Application No. 2009142976/10 mailed Jun. 14, 2012.

Abelev et al. "Sorosovsky obrazovatelniy zhurnal," *Osnovy Immuniteta*. No. 5. 1996. p. 6—English Abstract Provided.

Marri et al. "Physiological effects of alterstions in a primary structure," *Biokhimiya cheloveka*. vol. 1. Ch. 4. 1993. pp. 34, English Abstract Provided.

* cited by examiner

FUSION PROTEIN VACCINE

This application is a National Stage Application of PCT/SE2008/000270, filed 14 Apr. 2008, which claims benefit of Serial No. 0700919-4, filed 16 Apr. 2007 in Sweden, and U.S. Ser. No. 60/940,473, filed 29 May 2007 and which applications are incorporated herein by reference. To the extent appropriate, a claim of priority is made to each of the above disclosed applications.

FIELD OF INVENTION

The present invention relates to the fields of microbiology and vaccine technology, and concerns the development of a vaccine capable of conferring immunity to group B *Streptococcus* infections. More particularly, the present invention relates to a novel fusion protein which confers immunity to invasive strains of the group B *Streptococcus*. It further pertains to an isolated nucleotide sequence encoding said fusion protein; a vector; a host cell; a vaccine; and a method for preventing or treating a group B *Streptococcus* infection.

BACKGROUND OF THE INVENTION

Group B *Streptococcus* (*Streptococcus agalactiae*) (GBS) is the major cause of invasive bacterial infections, including meningitis, in the neonatal period. In the United States alone, there are now about 5000 cases per year of invasive disease caused by this bacterium. These infections have an overall mortality of about 10%, and many of the infants that survive have permanent neurological sequelae. In view of this, a large effort has been made to find methods of prevention and treatment and to analyze the mechanisms by which GBS cause infections.

The GBS can also cause mastitis in cows, a bovine disease that is of considerable economical importance. Development of a vaccine against GBS infections is therefore of interest also in veterinary medicine.

About 20% of all women are vaginal carriers of GBS, and vertical transmission from the maternal genital tract is probably the most common source of infection in neonatal disease caused by this bacterium. However, only about 1% of the infants that are colonized by the GBS at birth are afflicted by serious infection. Other factors than exposure to the bacterium during birth must therefore contribute to the development of neonatal disease.

Group B *streptococcal* strains are divided into nine serotypes (Ia, Ib, and II-VIII) based on the structure of the polysaccharide capsule (Baker, J Inf Dis 1990. 161: 917). The four "classical" serotypes Ia, Ib, II, and III occur in roughly equal proportions among strains in the normal flora, but type III is the clinically most important serotype, in particular because it causes most cases of meningitis.

Because the capsule is a known virulence factor, it has been studied in considerable detail, in particular in type III strains. Efforts have been made to develop a vaccine, in which the type III polysaccharide capsule would be an essential component.

EP 0 866 133 discloses a vaccine capable of protecting a recipient from infection caused by group B *Streptococcus*. The invention is directed to the use of a combination of a polysaccharide and a fragment of the epsilon protein. It further discloses that epidemiological data suggest that the type-specific capsule plays an important role in the immunity to group B *Streptococcus* infections (se page 7 line 2-3). Additionally, there are a number of different combinations between different proteins and the polysaccharide mentioned within the application but all the claims comprise a polysaccharide which shows the importance of that particular component. However, use of the polysaccharide capsule as a vaccine may give problems due to cross reactions with human tissues (Pritchard et al., Infect Immun 1992. 60: 1598). It would therefore be very valuable if one could develop a vaccine based on proteins rather than on polysaccharides.

The document Gravekamp et al., Infection and Immunity, December 1997, p 5216-5221 discloses the evaluation of the immunogenicity as well as protection of the number of repeats of the alpha (α) C protein as well as the N-terminal part alone. It was found that the immunogenicity decreased with increasing number of repeats (se FIG. 2B). However, it was also found in a protection assay that the antibodies against the repeat region were predominantly responsible for the protection compared to antibodies against the N-terminal region (see page 5219 left column, line 6 from the bottom, and page 5220 right column lines 26-29).

WO 9410317 describes the use of the alpha protein, a GBS surface protein, in the development of a conjugate vaccine. A drawback with this protein is that it usually is not expressed by type III strains, which are the cause of many serious GBS infections. Hence, a protective immunity against these strains will not be evoked by an alpha protein vaccine.

WO 9421685 describes the use of the Rib protein, a GBS surface protein, in the development of a vaccine. This protein elicits immunity when administered with alum. However, the Rib protein has the disadvantage that it does not evoke a protective immunity against all GBS strains.

Currently, as stated above, a vaccine suitable for prevention of GBS disease is not yet available, although much work has been devoted to this problem. Clearly, at present there is a long felt but unmet need to develop methods of prevention and treatment of GBS infections. Thus, there remains a need to explore vaccines strategies capable of eliciting protective immunity against a wide range of GBS stains.

Accordingly, it is a primary objective of the present invention to provide a vaccine capable of eliciting protective immunity against GBS infections.

It is a further objective of the present invention to provide a vaccine that elicits protective immunity against many clinically important GBS strains.

Another objective of the present invention is to provide a vaccine composed of a single fusion protein that elicits protective immunity against GBS infections. The single protein has several advantages over a vaccine composed of multiple proteins, e.g. cost of production and safety.

The means of accomplishing each of the above objectives as well as others will become apparent from the description of the invention which follows hereafter.

SUMMARY OF THE INVENTION

It has surprisingly been found that a fusion protein comprising two different non-immunodominant regions, such as the N-terminal region fragment from GBS Rib protein fused to the N-terminal region fragment from GBS alpha protein, i.e, a fusion between non-immunodominant regions in two different proteins expressed by two different strains of GBS, will give rise to a fusion protein which gives rise to a very efficient protection against infections with the two different bacterial strains, when the fusion protein is administrated to a mammal as a vaccine. This protection is conferred by antibodies.

In a first aspect the invention relates to a fusion protein comprising at least one first N-terminal region fragment of a group B *Streptococcus* surface protein or analogue, homologue, derivative or immunologically related amino acid sequence or fragments thereof, which is fused to at least one second N-terminal region fragment of a group B *Streptococcus* surface protein or analogue, homologue, derivative or immunologically related amino acid sequence or fragments thereof, wherein said first and second at least one N-terminal region fragments of group B *Streptococcus* surface proteins derive from different group B *Streptococcus* strains, and wherein said fusion protein is capable of eliciting protective immunity against group B *Streptococcus*.

A major advantage of the fusion protein of the invention is that it includes regions from the related surface proteins Rib and alpha, either of which is expressed by many clinically important strains of group B *Streptococcus*, and most importantly, it has been shown to elicit protective immunity against these clinically important strains.

The fusion protein has the advantage that it is immunogenic even without adjuvant, eliciting protective immunity against Rib- and alpha-expressing strains. Moreover, the fusion protein vaccine of the invention can be administered with alum, an adjuvant accepted for use in humans. In contrast, the recently described "universal vaccine" was only reported to work together with Freund's adjuvant, a strongly irritating component that cannot be used in human medicine (Maione, D. et al, Science 2005. 309:148-150).

Another advantage with the present invention is that a vaccine composition according to the invention can be composed of a single fusion protein and still elicit protective immunity against different GBS infections. This has several advantages over a vaccine composed of multiple proteins, e.g. a single protein is simpler, safer and cheaper to manufacture than a mixture containing multiple proteins.

More specifically, the present invention relates to said fusion protein; an isolated nucleotide sequence; a vector; a host cell; a vaccine; and a method for preventing or treating a group B *Streptococcus* infection.

The present invention will be described in more detail below, inter alia, with reference to the drawings.

DETAILED DESCRIPTION OF THE INVENTION

Figure 1:
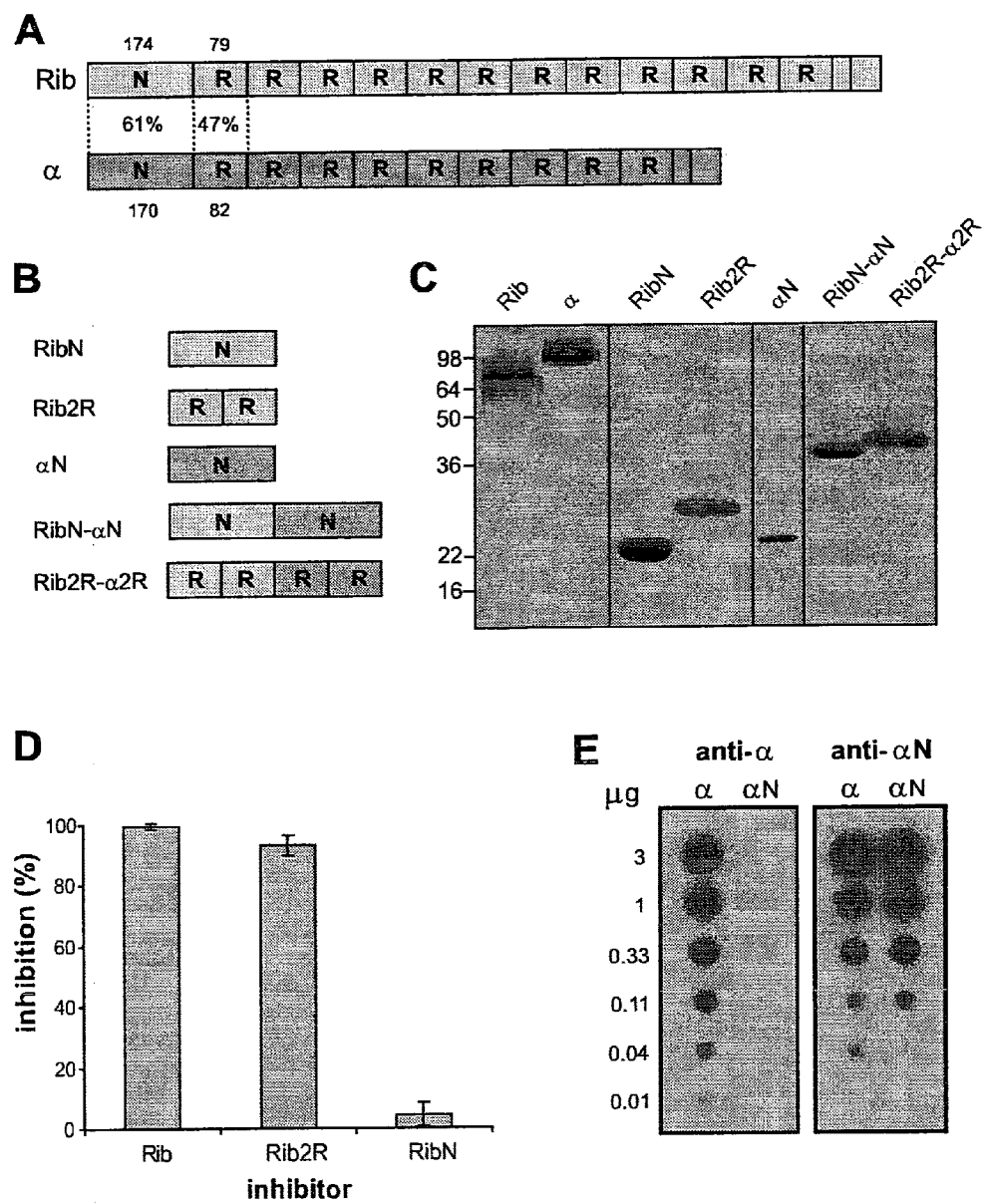
FIG. 1 shows proteins used in the examples. (A) shows the Rib and alpha proteins including their unique N-terminal regions (N-regions) and their long repeat regions (R-regions). The number of aa residues in different regions and residue identity are indicated. (B) Recombinant proteins derived from Rib and alpha. (C) Analysis of purified proteins by SDS-PAGE. (D) Inhibition test with mouse anti-Rib antibodies. (E) Dot-blot analysis.

The term "immunogenic" is intended to mean having the ability to elicit an immune response. The novel fusion protein of the invention is immunogenic and characterised by its ability to elicit a protective immune response against at least GBS containing the Rib- and the alpha-protein.

The term "analogue" is intended to mean those proteins related to the Rib- and alpha-proteins, wherein one or more amino acid residues of the Rib- or the alpha-protein (SEQ ID NO: 2 and 4) is replaced by another amino acid residue, providing that the overall functionality and immunogenic properties of the analogue protein or fusion protein are preserved. Such analogues may be naturally occurring, or may be produced synthetically or by recombinant DNA technology, for example, by mutagenesis of one or both of SEQ ID NO:1 and 3. Analogues of the fusion protein will possess at least one epitope capable of eliciting antibodies that react with the Rib-protein and at least one epitope that react with the alpha protein. Such an analogue can have overall homology or identity of at least 80% to the fusion protein shown in SEQ ID NO:6, such as 80-99% homology or identity, or any range therein.

Percent homology can be determined, for example, by comparing sequence information using the GAP computer program, version 6.0, available from the University of Wisconsin Genetics Computer Group (UWGCG). The GAP program utilizes the alignment method of Needleman and Wunsch (J Mol Biol 1970 48:443), as revised by Smith and Waterman (Adv Appl Math 1981 2:482). Briefly, the GAP program defines similarity as the number of aligned symbols (i.e., nucleotides or amino acids) which are similar, divided by the total number of symbols in the shorter of the two sequences. The preferred default parameters for the GAP program include: (1) a unitary comparison matrix (containing a value of 1 for identities and 0 for non-identities) and the weighted comparison matrix of Gribskov and Burgess (Nucl Acids Res 1986 14:6745), as described by Schwartz and Dayhoff, eds. (Atlas of Protein Sequence and Structure, National Biomedical Research Foundation, Washington, D.C. 1979, pp. 353-358); (2) a penalty of 3.0 for each gap and an additional 0.10 penalty for each symbol in each gap; and (3) no penalty for end gaps.

As used herein, "homologues" are related to said fusion protein or the Rib- and the alpha-protein from the *Streptococcal* species *agalactiae*, wherein one or more amino acid residues in the amino acid sequence (SEQ ID NO: 2 or 4) is replaced by another amino acid residue, providing that the overall functionality and immunogenic properties of the homologue protein are preserved. Such homologues may be naturally occurring, or may be produced synthetically or by recombinant DNA technology. Homologues of SEQ ID NO:2 or 4 will possess at least one epitope capable of eliciting antibodies that react with the Rib- or the alpha-protein. Such a homologue can have overall homology (i.e., similarity) or identity of at least 80% to the Rib- or the alpha-protein, such as 80-99% homology (i.e., similarity) or identity, or any range therein.

As used herein, a "derivative" is a polypeptide in which one or more physical, chemical, or biological properties have been altered. Such alterations include, but are not limited to:

amino acid substitutions, modifications, additions or deletions; alterations in the pattern of lipidation, glycosylation or phosphorylation; reactions of free amino, carboxyl, or hydroxyl side groups of the amino acid residues present in the polypeptide with other organic and non-organic molecules; and other alterations, any of which may result in changes in primary, secondary or tertiary structure.

The "fragments" of this invention will have at least one immunogenic epitope. The preferred fragments of this invention will elicit an immune response sufficient to prevent or ameliorate the severity of infection.

The term "pharmaceutical acceptable vehicle" is intended to mean any suitable acceptable excipient, adjuvants, carrier, diluent commonly used in pharmaceutical formulations.

The invention concerns a vaccine protecting against infections with group B *streptococcus* (GBS), the most important cause of life-threatening bacterial infections in newborns. The present invention is based on the inventor's knowledge and realization that a fusion protein derived from subregions in two large surface proteins of group B *Streptococcus*, the Rib and alpha proteins, elicit protective immunity.

With the long-term goal to develop a group B *Streptococcus* (GBS) vaccine based on a single component, the inventor analysed whether a fusion protein derived from Rib and alpha would elicit protective immunity. The large size of Rib and alpha, and the genetic instability of the repeat regions, implied that a fusion protein should be derived from subregions. However, the choice of subregions was not obvious, because protective epitopes are present in the repeat region of alpha and Rib. Surprisingly, the inventor has shown that a fusion protein derived from N-terminal regions had properties superior to one derived from other regions of these proteins, i.e. the repeats, and elicited good protective immunity.

In this specification, unless otherwise specified, "a" or "an" means "one or more".

Throughout the specification, any and all references are specifically incorporated into this patent application by reference.

The Fusion Protein

In a first aspect, the present invention relates to a fusion protein comprising at least a first N-terminal region fragment of a group B *Streptococcus* surface protein which is fused to at least a second N-terminal region fragment of a group B *Streptococcus* surface protein, wherein said first and second N-terminal region fragments of group B *Streptococcus* surface proteins derive from different group B *Streptococcus* surface proteins, and wherein said fusion protein is capable of eliciting protective immunity against group B *Streptococcus*.

Different *Streptococcus* surface proteins that could be comprised in the fusion protein of the present invention include but are not limited to group B *Streptococcus* Rib protein; group B *Streptococcus* alpha protein; group B *Streptococcus* beta protein; group B *Streptococcus* epsilon protein; and/or group B *Streptococcus* R28 protein.

According to one embodiment, the present invention relates to a fusion protein comprising an N-terminal region fragment of a group B *Streptococcus* Rib protein which is fused to an N-terminal region fragment of a group B *Streptococcus* alpha protein, wherein said fusion protein is capable of eliciting protective immunity against group B *Streptococcus*.

According to another embodiment the invention relates to a fusion, wherein said fusion protein comprises at least a first amino acid sequence SEQ ID NO:2 or analogue, homologue, derivative or immunological related amino acid sequence or fragments thereof fused to at least a second amino acid sequence SEQ ID NO:4 or analogue, homologue, derivative or immunological related amino acid sequence or fragments thereof. Said at least a first amino acid sequence comprises an amino acid sequence having at least 80, 85, 90, 95, 96, 97, 98 or 99% sequence identity with an amino acid sequence as shown in SEQ ID NO:2. Said at least a second amino acid sequence comprises an amino acid sequence having at least 80, 85, 90, 95, 96, 97, 98 or 99% sequence identity with an amino acid sequence as shown in SEQ ID NO:4. One example of a fusion protein is shown in SEQ ID NO:6, another example being a fusion protein which comprises a mixture of three or more amino acid sequences selected from the group consisting of SEQ ID NO:2 and SEQ ID NO:4, or parts thereof.

The group B *Streptococcus* Rib protein, also referred to in this specification as Rib and Rib protein, is a surface protein known in the art, and for example described in WO 9421685. The denotation "Rib" refers to: Resistance to proteases, immunity, and group B. The Rib protein was first isolated from a group B *streptococcal* strain of serotype III as a distinct 95 kDa protein. Protein Rib is expressed by almost all group B *streptococcal* strains of the clinically important serotype III, which cause most cases of meningitis, and by some strains of other serotypes such as II. Moreover, Rib is expressed by all strains of a hypervirulent clone of type III. A method has been devised to purify protein Rib and it has been demonstrated that antibodies to this protein protect against lethal infection with strains expressing protein Rib (for further details, such as DNA and protein sequences see WO 9421685).

The group B *Streptococcus* alpha protein, also referred to in this specification as alpha, alpha protein and alpha antigen, is a group B *Streptococcus* surface protein known in the art. WO 9410317 describes a conjugate vaccine composition comprising the alpha protein. The native group B *Streptococcus* alpha precursor protein as described in WO 9410317 has a molecular weight of 108 kDa. Cleavage of the putative signal sequence of 41 amino acids yields a mature protein of 104 kDa. (Note, however, that the signal sequence was subsequently shown to have a length of 56 amino acid residues: Stålhammar-Carlemalm et al., J Exp Med 177, 1593; 1993). The 20 kDa N-terminal region of the alpha antigen shows no homology to previously described protein sequences and is followed by a series of nine tandem repeating units that make up 74% of the mature protein. Each repeating unit (denoted herein as "R") is identical and consists of 82 amino acids with a molecular mass of about 8500 Daltons, which is encoded by 246 nucleotides. The C-terminal region of the alpha antigen contains a cell wall anchor domain motif present in a number of Gram-positive surface proteins.

Each of the Rib and alpha proteins of GBS includes a unique N-terminal region (N) and a long repeat (R) region. The proteins expressed by the GBS strains BM110 and A909 have 12 and 9 repeats, respectively, as indicated in FIG. 1A. The wall anchoring regions are located at the C-terminal ends.

The tandem repeats in Rib and alpha are identical within each protein, but not between the proteins, and vary in number between isolates. Except for this variation, the sequences of Rib and alpha are stable among strains. In spite of the considerable a.a. residue identity (FIG. 1A) the two proteins show little or no antigenic cross-reactivity.

The R28 protein is a Group B *Streptococcus* surface protein that confers protective immunity and promotes binding to human epithelial cells (Stålhammar-Carlemalm et al. *Molecular Microbiology* 1999. 33, 208-219).

The epsilon protein is a group B *streptococcal* alpha-protein-like protein (Creti et al. *Clin Microbiol.* 2004.42:1326-9).

The term "N-terminal region" in relation to the present invention refers to an N-terminus region (N) of a protein. Examples of amino acid sequences of the N-terminal regions of Rib and alpha are as indicated in SEQ ID NO: 2 and SEQ ID NO: 4.

For the purpose of the present invention the term "fusion protein" refers to an assembly of two or more protein regions, or fragments thereof, comprising for example an N-terminal region fragment of a group B *Streptococcus* Rib protein and an N-terminal region fragment of a group B *Streptococcus* alpha protein. For example there might be one N-terminal region fragment of the Rib- and one N-terminal region fragment of the alpha-protein, or 2, 3, 4 or 5 N-terminal region fragments of the Rib- and the alpha-proteins, wherein the numbers of fragments from the two proteins are not equal.

Examples of N-terminal region fragments of a group B *Streptococcus* Rib protein and N-terminal region fragments of a group B *Streptococcus* alpha protein, include peptides encoding native amino acid sequences of N-terminal regions of natural alpha and Rib proteins (for example SEQ ID NO: 2 and SEQ ID NO: 4), or may be functional derivatives of native sequences of these regions wherein these functional derivatives retain their ability to elicit protective immunity against the group B *Streptococcus*. The term functional derivatives is intended to include parts of sequences and fragments of the N-terminal regions; it is also intended to include variants of the natural proteins (such as proteins having changes in amino acid sequence but which retain the ability to elicit an immunogenic, virulence or antigenic property as exhibited by the natural molecule), for example, with altered flanking sequence.

It is encompassed that N-terminal region fragments from different strains of group B *Streptococcus* may be used according to the present invention. This will imply slight variability in the sequence of the N-terminal region fragments but would not alter the biological properties and their functional ability to elicit protective immunity. For example, group B *Streptococcus* alpha and Rib antigens isolated from different strains of group B *Streptococcus*, than those disclosed in SEQ ID NO: 2 and SEQ ID NO: 4 are intended to be within the scope of the invention.

The combination of polypeptides to provide a fusion protein can be accomplished by several means, e.g.: chemically by coupling, conjugation or cross-linking, either directly or through an intermediate structure; physically by coupling through capture in or on a macromolecular structure; or by molecular biological fusion, through the combination of recombinant nucleic acid molecules which comprise fragments of nucleic acid capable of encoding each of the two, such that a single continuous expression product is finally produced.

For the purpose of the present invention the term "protein" refers to a molecular chain of amino acids. A protein is not of a specific length and can, if required, be modified in vivo or in vitro, by, for example, glycosylation, amidation, carboxylation or phosphorylation. Inter alia, peptides, oligopeptides and polypeptides are included within the definition. The protein or peptide can be of natural or synthetic origin. In this context a fusion protein is intended to mean two or more polypeptides covalently linked to each other either directly or indirectly by several means such as those mentioned above. The term "fused" means to create a fusion protein as mentioned above.

Group B *streptococcal* strains, also referred herein as GBS, are well known and may be isolated from the blood of infected human beings. GBS is the most common cause of neonatal sepsis in the United States and is responsible for about 5000 cases per year.

The denotation "Group B *streptococcal*" derives from the fact that *Streptococci* have been divided into immunological groups based upon the presence of specific carbohydrate antigens on their cell surfaces. At present, groups A through 0 are recognized (Davis, B. D. et al., In: Microbiology, 3rd. Edition, page 609, (Harper & Row, 1980).

The term "protective immunity" in relation to the present invention refers to the ability of serum antibodies and/or cytotoxic T cell response induced during immunization to protect (partially or totally) against disease caused by an infectious agent, such as a group B *Streptococcus*. That is, a vertebrate immunized by the vaccines of the invention will experience limited growth and spread of group B *Streptococcus*. To determine whether protective immunity is induced by a fusion protein or vaccine, techniques well known for a person skilled in the art can be used. For example, to determine whether immunization with a fusion protein or vaccine of the invention induces protective immunity against group B *Streptococcus* infection, immunized test animals can be challenged with group B *Streptococcus* and growth and spread of the group B *Streptococcus* is measured. For example to determine whether protective immunity is induced, methods in accordance with the methods described in the examples below can be used.

In one embodiment of the invention, the fusion protein further comprises an N-terminal region fragment of a group B *Streptococcus* R28 protein (Gene bank acc no: AAD39085.1) and/or an N-terminal region fragment of a group B *Streptococcus* epsilon protein.

In one embodiment of the invention, the fusion protein of the present invention comprises repeating peptide sequences of the N-terminal region fragments of the group B *Streptococcus* proteins (i.e. alpha and Rib).

According to one embodiment of the invention, the fusion protein comprises an amino acid sequence having of at least 80%, 85%, preferably 90%, more preferably 95% sequence identity to the amino acid sequence as shown in SEQ ID NO:6.

The term "sequence identity" indicates a quantitative measure of the degree of homology between two amino acid sequences of equal length or between two nucleotide sequences of equal length. If the two sequences to be compared are not of equal length, they must be aligned to best possible fit. Sequence identity can, for example, be calculated by the BLAST program e.g. the BLASTP program or the BLASTN program (Pearson W. R and D. J. Lipman (1988) PNAS USA 85:2444-2448) (www.ncbl.nlm.nlh.gov/BLAST).

According to a further embodiment of the invention, the fusion protein comprises an amino acid sequence as shown in SEQ ID NO:6.

Isolated DNA & Expression Systems

In a second aspect according to the present invention, there is provided an isolated nucleotide sequence/DNA molecule comprising a nucleotide sequence/DNA sequence which encodes for the fusion protein according to the invention. One example is a nucleotide sequence comprising at least a first nucleotide sequence as shown in SEQ ID NO:1 or fragments thereof fused to at least a second nucleotide sequence as shown in SEQ ID NO:3 or fragments thereof.

Further, there is provided a recombinant expression system including vectors and host cells.

A wide variety of expression host/vector combinations may be employed in expressing the nucleotide sequences of this invention. Useful expression vectors for eukaryotic hosts include, for example, vectors comprising expression control sequences from SV40, bovine papilloma virus, adenovirus, adeno-associated virus, cytomegalovirus, and retroviruses. Useful expression vectors for bacterial hosts include bacterial plasmids, such as those from E. coli, including pBluescript, pGEX2T, pUC vectors, col E1, pCR1, pBR322, pMB9 and their derivatives, wider host range plasmids, such as RP4, phage DNAs, e.g., the numerous derivatives of phage lambda, e.g., lambda GT10 and lambda GT11, NM989, and other DNA phages, such as M13 and filamentous single stranded DNA phages. Useful expression vectors for yeast cells include the 2.mu. plasmid and derivatives thereof. Useful vectors for insect cells include pVL 941.

In addition, any of a wide variety of expression control sequences may be used in these vectors to express the nucleotide sequences/DNA sequences of this invention. Useful expression control sequences include the expression control sequences associated with structural genes of the foregoing expression vectors. Examples of useful expression control sequences include, for example, the early and late promoters of SV40 or adenovirus, the lac system, the trp system, the TAC or TRC system, the T3 and T7 promoters, the major operator and promoter regions of phage lambda, the control regions of fd coat protein, the promoter for 3-phosphoglycerate kinase or other glycolytic enzymes, the promoters of acid phosphatase, e.g., Pho5, the promoters of the yeast alpha-mating system and other constitutive and inducible promoter sequences known to control the expression of genes of prokaryotic or eukaryotic cells or their viruses, and various combinations thereof.

Host cells transformed with the foregoing vectors form a further aspect of this invention. A wide variety of unicellular host cells are useful in expressing the nucleotide sequences/DNA sequences of this invention. These hosts may include well known eukaryotic and prokaryotic hosts, such as both gram negative and gram positive strains, such as strains of E. coli, Pseudomonas, Bacillus, Streptomyces, streptococcus, staphylococcus, lactobacillus, aspergillus, shigella, salmonella, listeria, fungi, yeast, insect cells such as Spodoptera frugiperda (SF9), animal cells such as CHO and mouse cells, African green monkey cells such as COS 1, COS 7, BSC 1, BSC 40, and BMT 10, human cells, and plant cells in tissue culture. Preferred host organisms include bacteria such as E. coli and B. subtilis, and mammalian cells in tissue culture.

It should, of course, be understood that not all vectors and expression control sequences will function equally well to express the nucleotide sequences/DNA sequences of this invention. Neither will all hosts function equally well with the same expression system. However, one of skill in the art may make a selection among these vectors, expression control sequences and hosts without undue experimentation and without departing from the scope of this invention. For example, in selecting a vector, the host must be considered because the vector must replicate in it. The vector's copy number, the ability to control that copy number, and the expression of any other proteins encoded by the vector, such as antibiotic markers, should also be considered. In selecting an expression control sequence, a variety of factors should also be considered. These include, for example, the relative strength of the sequence, its controllability, and its compatibility with the nucleotide sequences/DNA sequences of this invention, particularly as regards potential secondary structures. Unicellular hosts should be selected by consideration of their compatibility with the chosen vector, the toxicity of the product coded for by the nucleotide sequences/DNA sequences of this invention, their secretion characteristics, their ability to fold the protein correctly, their fermentation or culture requirements, and the ease of purification from them of the products coded for by the nucleotide sequences/DNA sequences of this invention. Within these parameters, one of skill in the art may select various vector/expression control sequence/host combinations that will express the nucleotide sequences/DNA sequences of this invention on cultivation or in large-scale animal culture.

The polypeptides encoded by the nucleotide sequences/DNA sequences of this invention may be isolated from the microbial culture or cell culture and purified using any of a variety of conventional methods including: liquid chromatography such as normal or reversed phase, using HPLC, FPLC and the like; affinity chromatography (such as with inorganic ligands or monoclonal antibodies); ion exchange chromatography, size exclusion chromatography; immobilized metal chelate chromatography; gel electrophoresis; and the like. One of skill in the art may select the most appropriate isolation and purification techniques without departing from the scope of this invention.

In addition, the polypeptides of this invention may be generated by any of several chemical techniques. For example, they may be prepared using the solid-phase synthetic technique originally described by R. B. Merrifield (J Am Chem Soc 1963 83:2149-54), or they may be prepared by synthesis in solution. A summary of peptide synthesis techniques may be found in E. Gross & H. J. Meinhofer, 4 The Peptides: Analysis Synthesis, Biology; Modern Techniques Of Peptide And Amino Acid Analysis, John Wiley & Sons, (1981); and M. Bodanszky, Principles Of Peptide Synthesis, Springer-Verlag (1984).

The preferred compositions and methods of this invention comprise polypeptides having enhanced immunogenicity. Such polypeptides may result when the native forms of the polypeptides or fragments thereof are modified or subjected to treatments to enhance their immunogenic character in the intended recipient. Numerous techniques are available and well known to those of skill in the art which may be used, without undue experimentation, to substantially increase the immunogenicity of the polypeptides herein disclosed. For example, the polypeptides may be modified by coupling to dinitrophenol groups or arsanilic acid, or by denaturation with heat and/or SDS. Particularly if the polypeptides are small polypeptides synthesized chemically, it may be desirable to couple them to an immunogenic carrier. The coupling of course, must not interfere with the ability of either the polypeptide or the carrier to function appropriately. For a review of some general considerations in coupling strategies, see Antibodies, A Laboratory Manual, Cold Spring Harbor Laboratory, ed. E. Harlow and D. Lane (1988). Useful immunogenic carriers are well known in the art. Examples of such carriers are keyhole limpet hemocyanin (KLH); albumins such as bovine serum albumin (BSA) and ovalbumin, PPD (purified protein derivative of tuberculin); red blood cells; tetanus toxoid; cholera toxoid; agarose beads; activated carbon; or bentonite.

Expression may also be performed in so-called cell-free expression systems. Such systems comprise all essential factors for expression from an appropriate recombinant nucleic acid, operably linked to a promoter that will function in that particular system.

The nucleotide sequences/DNA sequence of the N-terminal regions of Rib and alpha are as indicated in SEQ ID NO:

1 and SEQ ID NO: 3, and the nucleotide sequences/DNA sequence of the fusion protein used in the examples below is as shown in SEQ ID NO:5.

In one embodiment the invention relates to a method of producing said fusion protein comprising the steps of providing a host cell as disclosed above comprising a nucleotide sequence as described above, multiplying said host cell in a suitable host medium well-known for a person skilled in the art, purifying said fusion protein using one or more of the above mentioned techniques and obtaining said fusion protein, which further may be used for the preparation of a vaccine as described below.

Vaccine Compositions

In a third aspect according to the present invention, there is provided a vaccine comprising the fusion protein of the invention and a pharmaceutically acceptable vehicle.

The vaccine composition of the present invention may, in addition to the fusion protein, comprise other pharmacologically acceptable ingredients such as salts, buffers, immunoactive components, adjuvants, wetting agents, emulsifying and suspending agents, or sweetening, flavouring, perfuming agents, or other substances which are desirable for improving the efficacy of the composition. A composition is said to be "pharmacologically acceptable" if its administration can be tolerated by a recipient individual.

A multivalent vaccine may also be prepared by combining the fusion protein with other components, including but not limited to diphtheria toxoid or tetanus toxoid, or polysaccharides, using techniques known in the art.

Other examples of the preferred proteins of a multivalent vaccine of the present invention include additional surface proteins of the group B *Streptococcus*, or their equivalents, such as the R28 protein and the epsilon protein.

In one embodiment, the vaccine composition of the present invention comprises a fragment of a group B *Streptococcus* R28 protein and/or a fragment of a group B *Streptococcus* epsilon protein.

Methods for the preparation and formulation of vaccine compositions are well known to those skilled in the art. The choice of ingredients will for instance vary depending on the administration route of the composition. For example compositions for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Carriers or occlusive dressings can be used to increase skin permeability and enhance antigen absorption. Liquid dosage forms for oral administration may generally comprise a liposome solution containing the liquid dosage form. Suitable forms for suspending liposomes include emulsions, suspensions, solutions, syrups, and elixirs containing inert diluents commonly used in the art, such as purified water.

The vaccine composition of the present invention may comprise an additional immunoactive component. The additional immunoactive component may be an antigen, an immune enhancing substance, and/or a vaccine; either of these may comprise an adjuvant.

Adjuvants are substances that can be used to specifically augment a specific immune response. Normally, the adjuvant and the composition are mixed prior to presentation to the immune system, or presented separately, but into the same site of the animal or human being immunized. Adjuvants can be loosely divided into several groups based upon their composition. These groups include oil adjuvants (for example, Freund's complete and incomplete), mineral salts for example, A1K $(SO_4)_2$, AlNa $(SO_4)_2$, AlNH$_4$ $(SO_4)$. silica, kaolin, and carbon), polynucleotides (for example, poly IC and poly AU acids), and certain natural substances (for example, wax D from *Mycobacterium tuberculosis*, as well as substances found in *Corynebacterium parvum*, or *Bordetella pertussis*, and members of the genus *Brucella*. Among those substances particularly useful as adjuvants are saponins such as, for example, Quil A. Examples of materials suitable for use in vaccine compositions are provided in Remington's Pharmaceutical Sciences (Osol, A, Ed, Mack Publishing Co, Easton, Pa., pp. 1324-1341 (1980).

In a further embodiment, the fusion protein of the invention may be used as carrier for a polysaccharide in a conjugate vaccine. In this embodiment the vaccine comprises a protein, i.e. the fusion protein, conjugated to a polysaccharide (such as a capsular polysaccharide).

The use of a polypeptide, protein or fusion protein as a carrier for a polysaccharide in a conjugate vaccine is well known in the art, see for example U.S. Pat. No. 6,855,321, WO 9410317 and U.S. Pat. No. 4,496,538).

By polysaccharide is meant any linear or branched polymer consisting of monosaccharide residues, usually linked by glycosidic linkages, and thus includes oligosaccharides. Preferably, the polysaccharide will contain between 2 and 50 monosaccharide unites, more preferably between 6 and 30 monosaccharide units.

The polysaccharide component may be based on or derived from polysaccharide components of the polysaccharide capsule from many Gram positive and Gram negative bacterial pathogens such as *H. influenzae, N. meningitidis* and *S. pneumoniae*. Other bacteria from which polysaccharide components may be conjugated to the carrier proteins of the present invention include *Staphylococcus aureus, Klebsiella, Pseudomonas, Salmonella typhi, Pseudomonas aeruginosa*, and *Shigella dysenteriae*. Polysaccharide components suitable for use according to this aspect of the present invention include the Hib oligosaccharide, lipopolysaccharide from *Pseudomonas aeruginosa* (Seid and Sadoff, 1981), lipopolysaccharides from *Salmonella* (Konadu et al., 1996) and the O-specific polysaccharide from *Shigella dysenteriae* (Chu et al, 1991). Other polysaccharide components suitable for use in accordance with the present invention will be well-known to those skilled in the art.

Fragments of bacterial capsular polysaccharide may be produced by any suitable method, such as by acid hydrolysis or ultrasonic irradiation (Szn et al, 1986). Other methods of preparation of the polysaccharide components will be well known to those of skill in the art.

In one embodiment of the present invention, the polysaccharide is a capsular polysaccharide derived from group B *Streptococcus*, or their equivalents.

The polysaccharide component of the conjugate vaccine should preferably be coupled to the carrier protein by a covalent linkage. A particularly preferred method of coupling polysaccharide and protein is by reductive amination. Other methods include: activation of the polysaccharide with cyanogen bromide followed by reaction with adipic acid dihydrazide (spacer) and by conjugation to carboxide groups of carrier protein using soluble carbodiimides (Shneerson et al, 1986); functionalisation of the carrier protein with adipic acid dihydrazide followed by coupling to cyanogen bromide activated polysaccharides (Dick et al, 1989); chemical modification of both the carrier protein and the polysaccharide followed by their coupling (Marburg et at, 1986; Marburg et al, 1987 and 1989).

The polysaccharide molecule may be coupled to the carrier protein by a spacer molecule, such as adipic acid. This spacer molecule can be used to facilitate the coupling of protein to polysaccharide. After the coupling reaction has been performed, the conjugate may be purified by diafiltration or other known methods to remove unreacted protein or polysaccharide components.

If the polysaccharide is derived from a bacterial pathogen different from GBS, the conjugate may elicit immunity against two or more pathogens, e.g. multiple types of bacteria. This is a potentially important application of the fusion protein. For the preparation of a conjugate vaccine, it would be a considerable advantage that the protein part is composed of a single fusion protein.

It is apparent to an artisan of skill in the art that vaccine composition of the present invention may comprise other substances or compounds not mentioned above, such as other diluents, emulsifying or stabilizing agents, or other proteins or polysaccharides. Such substances or compounds should confer desired properties to the composition.

Methods for Preventing and Treating Group B *Streptococcus* Infection

In further aspects according to the present invention, methods for preventing or treating an infection caused by a group B *Streptococcus* are provided. These methods comprise administering to an individual a pharmaceutically effective amount of the vaccine of the invention. There is also, according to the present invention, provided a use of the immunogenic composition of the invention for the manufacture of a vaccine for preventing or treating an infection caused by a group B *Streptococcus*.

Maternal immunoprophylaxis with a vaccine, for protecting against infection to group B *Streptococcus* both in the mother and in the young infant, has long been proposed as a potential route.

The terms "preventing or treating" in its various grammatical forms in relation to the present invention refer to preventing, curing, reversing, attenuating, alleviating, ameliorating, inhibiting, minimizing, suppressing, or halting (1) the deleterious effects of a disorder associated with group B *Streptococcus* infection, (2) disorder progression, or (3) disorder causative agent (group B *Streptococcus*). Further, the terms "preventing or treating" are contemplated to include the creation of total or partial immunity of the individual to group B *Streptococcus* infection.

According to one embodiment, the method for preventing or treating comprises administering to a female an effective amount of the vaccine of the invention capable of conferring immunity to group B *Streptococcus* infection to an unborn offspring of said female. According to this embodiment, the vaccine is administered to a non-pregnant female or to a pregnant female, under conditions of time and amount sufficient to cause the production of antibodies which serve to protect both the female and a fetus or newborn (via passive transfer of antibodies across the placenta).

In a further embodiment, the method for preventing or treating an infection caused by a group B *Streptococcus* comprises administering to an individual an effective amount of an antisera elicited from the exposure of a second individual to a vaccine of the invention. According to this embodiment, resistance to group B *Streptococcus* is conferred to the individual by passive immunization, i.e., the vaccine is provided to a host (i.e. a human or mammal) volunteer, and the elicited antisera is recovered and directly provided to a recipient suspected of having an infection caused by a group B *Streptococcus*. It is contemplated that such antisera could be administered to a pregnant female (at or prior to parturition), under conditions of time and amount sufficient so that the antisera would serve to protect either the fetus or newborn (via passive incorporation of the antibodies across the placenta).

The vaccine or antisera of the present invention may, thus, be provided either prior to the onset of infection (so as to prevent or attenuate an anticipated infection) or after the initiation of an actual infection.

The vaccine composition or the antisera according to the invention may be administered to humans or animals, including mammals and birds, such as rodents (mouse, rat, guinea pig, or rabbit); birds (turkey, hen or chicken); other farm animals (cow, horse, pig or piglet); pets (dog, cat and other pets); and humans. While many animals may be treated with the preparation of the invention, a preferred individual for treatment is a human or commercially valuable animal and livestock.

The vaccine composition or the antisera according to the invention can be administered to an individual according to methods known in the art. Such methods comprise application e.g. parenterally, such as through all routes of injection into or through the skin: e.g. intramuscular, intravenous, intraperitoneal, intradermal, mucosal, submucosal, or subcutaneous. Also, they may be applied by topical application as a drop, spray, gel or ointment to the mucosal epithelium of the eye, nose, mouth, anus, or vagina, or onto the epidermis of the outer skin at any part of the body. Other possible routes of application are by spray, aerosol, or powder application through inhalation via the respiratory tract. In this last case the particle size that is used will determine how deep the particles will penetrate into the respiratory tract. Alternatively, application can be via the alimentary route, by combining with the food, feed or drinking water e.g. as a powder, a liquid, or tablet, or by administration directly into the mouth as a: liquid, a gel, a tablet, or a capsule, or to the anus as a suppository. The vaccine may also be administered in the form of a DNA vaccine.

Many different techniques exist for the timing of the immunizations. It is possible to use the compositions of the invention more than once to increase the levels and diversities of expression of the immunoglobulin repertoire expressed by the immunized animal. Typically, if multiple immunizations are given, they will be given one to two months apart.

The term "effective amount" in relation to the present invention refers to that amount which provides a therapeutic effect for a given condition and administration regimen. This is a predetermined quantity of active material calculated to produce a desired therapeutic effect in association with the required additives and diluents; i.e., a carrier, or administration vehicle. Further, it is intended to mean an amount sufficient to reduce and most preferably prevent a clinically significant deficit in the activity and response of the host. Alternatively, a therapeutically effective amount is sufficient to cause an improvement in a clinically significant condition in a host. As is appreciated by those skilled in the art, the amount of a compound may vary depending on its specific activity. Suitable dosage amounts may contain a predetermined quantity of active composition calculated to produce the desired therapeutic effect in association with the required diluents; i.e., carrier, or additive. Further, the dosage to be administered will vary depending on the active principle or principles to be used, the age, weight etc of the individual to be treated.

Generally, the dosage will consist of an initial injection, most probably with adjuvant, of about 0.01 to 10 mg, and preferable 0.1 to 1.0 mg, fusion protein antigen per individual, followed most probably by one or maybe more booster injections. Preferably, boosters will be administered at about 1 and 6 months after the initial injection.

EXAMPLES

In order that this invention may be better understood, the following examples are set forth. It should be understood, however, that the following examples are given to illustrate the present invention and the invention is not intended to be limited to the specific conditions and details described in these examples.

In the examples below, the following group B *Streptococcus* (GBS) strains were used: A909 (type Ia) SB35sed1 (type Ib); 1954/92 (type II); and BM110 (type III) (Larsson et al. *Infect. Immun.* 1996. 64:3518-3523; Stålhammar-Carlemalm et al. *J. Exp. Med.* 1993. 177:1593-1603). Strain BM110 is a member of the hypervirulent ST-17 clone. All GBS strains were grown in Todd-Hewitt broth at 37° C. without shaking.

All strains referred to herein are obtainable from the inventors at the University of Lund and the Lund University Hospital (Doctor Gunnar Lindahl, Department of Medical Microbiology, Sölvegatan 23, SE-22362 Lund, Sweden).

Example 1

Construction of Rib- and Alpha-Negative Bacterial Mutants

A Rib-negative mutant was derived from BM110. A ~7 kb fragment, harbouring the rib gene and flanking sequences, was subcloned into pJRS233 (Perez-Casal et al, *Mol. Microbiol.* 1993. 8:809-819.). The rib gene was deleted by inverse PCR and replaced with a kanamycin resistance cassette. After transformation into BM110, a Rib-negative mutant was isolated by homologous recombination (Perez-Casal, J. et al, 1993). The entire rib gene is absent from this mutant, unlike one previously described (Waldemarsson et al. *J. Bacteriol.* 2006. 188:378-388). The structure of the mutant was confirmed by PCR. The mutant lacked reactivity with anti-Rib serum but was not affected in expression of capsule. An alpha-negative mutant of A909 was constructed by similar techniques. This mutant lacked reactivity with anti-alpha serum but was not affected in expression of capsule or beta protein.

Example 2

Construction of Fusion Proteins and Other Derivatives of Rib and Alpha

In the examples described herein, the intact proteins and a series of recombinant proteins were employed (see FIG. 1B). Fragments of the Rib gene (SEQ ID NO:1) in BM110 and the bca gene, encoding the alpha protein (SEQ ID NO:3) in A909 were cloned into pGEX-6P-2 (Amersham) and used for preparation of GST-fusions. After removal of the GST moiety, the purified derivatives had the N-terminal sequence GPLGS. RibN and Rib2R correspond to aa residues 1-174 and 175-332, respectively, of Rib, and alphaN corresponds to residues 1-170 of alpha (numbering of Wästfelt et al. *J. Biol. Chem.* 1996. 271:18892-18897). RibN-alphaN contains aa 1-174 of Rib and aa 1-170 of alpha, while Rib2R-alpha2R 12 contains aa 175-332 of Rib and aa 171-334 of alpha. Due to the procedures used, each fusion protein included the sequence EF between the two regions. Rib and alpha were purified from BM110 and A909, respectively.

Example 3

Analysis of Purified Proteins

FIG. 1C shows the analysis of purified proteins by SDS-PAGE. The figure is combined from two gels. Numbers to the left indicate molecular mass in kDa. Because Rib and alpha migrate aberrantly in gels, the apparent sizes of the proteins do not exactly correspond to those deduced from a.a. sequences.

Example 4

Test of Immunodominance of the Repeat Regions of Rib and Alpha

Rabbit antisera were raised by s.c. immunization with ~35 µg protein in CFA, followed by two boosters with ~18 µg protein in IFA. Mice were immunized s.c. with 25 µg protein with or without adjuvant, as indicated, boosted after 4 wk with 12 µg protein, and bled two wk later. For the CFA mice, the booster was administered with IFA.

Antibody binding and inhibition tests (FIG. 1D) were performed essentially as described (Stålhammar-Carlemalm et al, *J. Exp. Med.* 1993. 177:1593-1603; Wästfelt et al. *J. Biol. Chem.* 1996. 271:18892-18897) to analyse whether mouse anti-Rib antibodies, elicited with alum as adjuvant, were directed against the N-terminal region and/or the repeat region. The antibodies, elicited with alum as adjuvant, were used to detect pure Rib immobilized in microtiter wells and binding was inhibited by addition of the pure protein indicated (2 µg). Bound rabbit antibodies were detected with radiolabeled protein G, and bound mouse antibodies were detected by incubation with rabbit anti-mouse Ig followed by radiolabeled protein G. Binding was calculated in % of protein G bound at the lowest antiserum dilution. The sensitivity of inhibition tests (FIG. 1D) was optimized by using a coating solution at 0.05 µg/ml and mouse serum diluted 1000-fold. All tests were performed at least three times, and SDs are indicated. For dot blot analysis, membranes were incubated with the mouse serum indicated and bound antibodies were detected by incubation with rabbit anti-mouse Ig, followed by radiolabeled protein G and autoradiography.

Binding to Rib was completely inhibited by Rib, as expected, and almost complete inhibition was also observed with Rib2R, while RibN had a very small effect. Thus, almost all antibodies were directed against the repeats. The inhibition by Rib2R was not unspecific, because it did not inhibit binding of antibodies to an unrelated GBS antigen (data not shown).

In the alpha system, a dot-blot analysis showed that anti-alpha reacted with intact alpha but not with alphaN (FIG. 1 E, left). The lack of reactivity of alphaN was not an inherent property of that construct, because anti-alphaN reacted with both alpha and alphaN (FIG. 1 E, right).

The reason for the immunodominance of the repeat regions in Rib and alpha is not known. Multivalent interactions between the repeats and Ig receptors on B cells may contribute, but Rib and alpha are not T-cell-independent antigens, because they elicit IgG responses. Of note, the poor immune response to the $NH_2$-terminal regions was not due to masking, because these regions are available to antibodies (see below).

Example 5

Passive Vaccination

Because antibodies to Rib and alpha are directed almost exclusively against the repeats and are protective, it would appear that a fusion protein vaccine should be derived from the repeats. However, the available data did not exclude that the isolated N-terminal regions might be more protective than the repeats and would be suitable for the construction of a fusion protein. To analyze this hypothesis, we used the Rib system to directly compare the protective ability of antibodies directed against the N-terminal region or the repeats. The analysis employed rabbit antibodies elicited by RibN or Rib2R and a mouse model of passive vaccination.

Passive vaccinations were performed as described (Stålhammar-Carlemalm et al, *J. Exp. Med.* 1993. 177:1593-1603), using C3H/HeN mice, rabbit antiserum, and an $LD_{90}$ dose of log-phase bacteria ($10^5$-$10^6$ CFU, depending on the strain used). Survival was recorded during a 96 h period. For active vaccinations, mice were immunized s.c. with 10 μg protein, mixed with alum. A 5 μg booster was given after 4 wk, with alum. Control mice received PBS and alum. Two wk after the booster the mice were challenged with an $LD_{90}$ dose of bacteria and survival was recorded. All experiments were approved by the local review board on animal studies.

Figure 2:
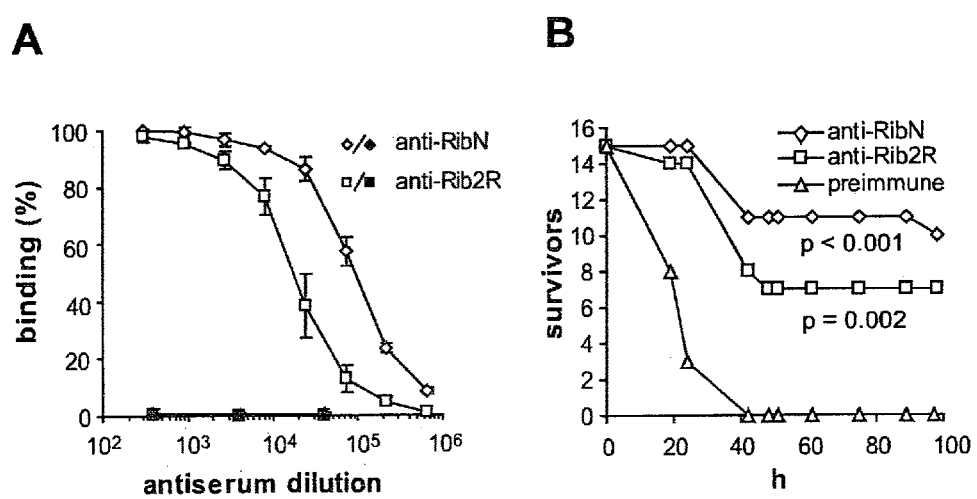
FIG. 2 shows data from studies with passive immunization. (A) Reactivity of rabbit antisera against RibN or Rib2R with bacteria of the Rib expressing strain BM110 (open symbols) or its Rib-negative mutant (closed symbols). (B) Passive vaccination of mice with rabbit anti-RibN or anti-Rib2R.

The antibodies reacted with Rib-expressing bacteria, but not with a Rib-negative mutant, demonstrating that they recognized epitopes exposed on the native form of Rib (FIG. 2 A). Because anti-RibN had ~7-fold higher titer than anti-Rib2R it was diluted accordingly, to allow direct comparisons in the mouse model. In this model, each antiserum protected against lethal infection (FIG. 2 B), and the diluted anti-RibN protected at least as well as the undiluted anti-Rib2R. The p values refer to comparisons with the pre-immune control at 96 h. The results in the Rib system suggested that a fusion protein derived from the N-terminal regions of Rib and alpha should be compared with one derived from the repeats. However, it was not obvious that a fusion protein derived from the N-terminal regions was needed, because these regions exhibit 61% residue identity (FIG. 1A), suggesting that they might cross-react. Cross-reactivity could have gone unnoticed in previous studies, which employed antibodies against the intact proteins, i.e. antibodies directed mainly against the repeats.

Figure 3:
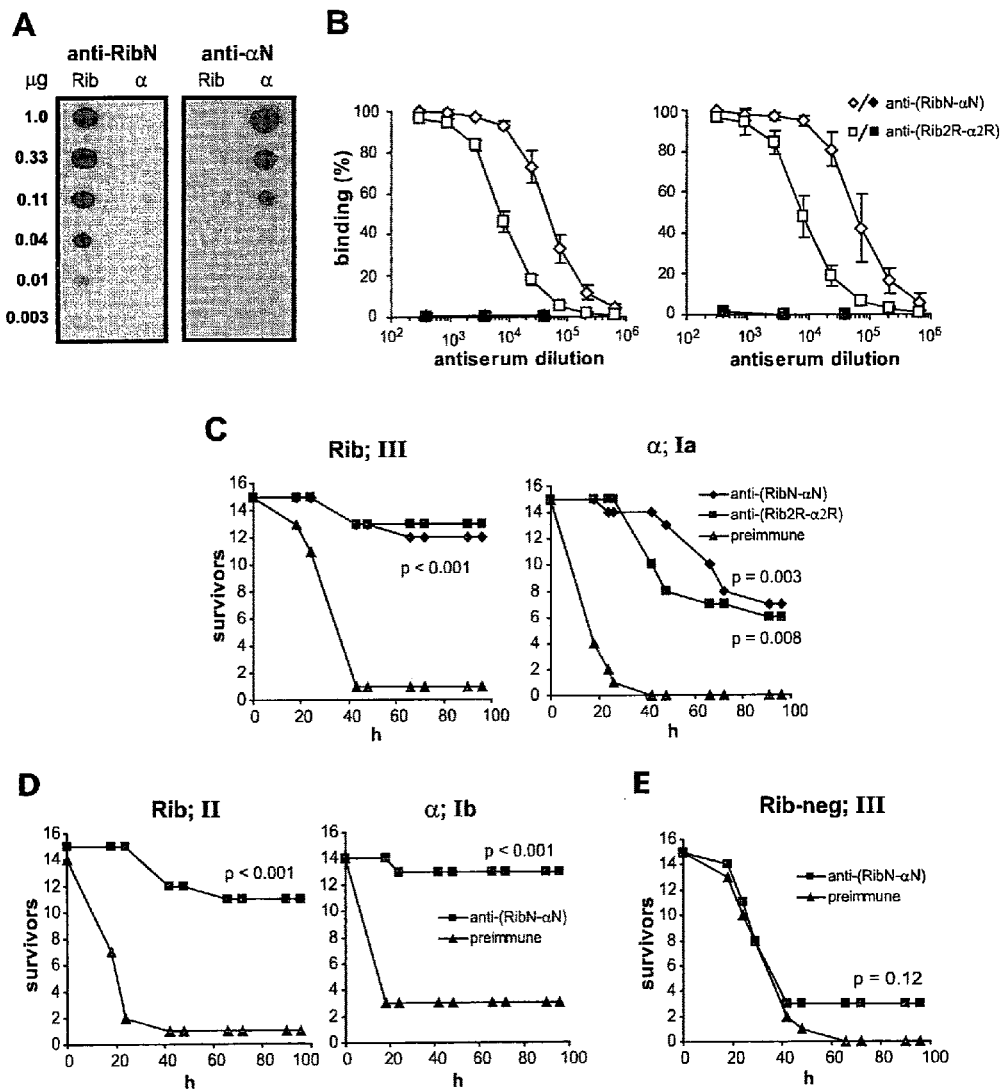
FIG. 3 shows (A) Analysis of cross-reactivity between the N-terminal regions of Rib and alpha. (B) Characterization of rabbit antibodies against RibN-alphaN and Rib2R-alpha2R. (C) Passive vaccination of mice with antibodies to the two fusion proteins, followed by challenge with the Rib expressing type III strain BM110 or the alpha-expressing type Ia strain A909. (D) Passive vaccination with anti-(RibN-alphaN) followed by challenge with a Rib expressing type II strain or an alpha-expressing type Ib strain. (E) Passive vaccination with anti-(RibN-alphaN), followed by challenge with a Rib-negative BM110 mutant.

This hypothesis was analyzed with anti-RibN and anti-alphaN (FIG. 3 A). Each antiserum reacted with whole bacteria of the Rib-expressing strain BM110 (left, open symbols) but not with a Rib-negative mutant (left, closed symbols). Similarly, each antiserum reacted with bacteria of the alpha-expressing strain A909 (right, open symbols) but not with an alpha-negative mutant (right, closed symbols). Similar data were obtained with two rabbit sera of each type. This indicates that the N-terminal regions lack crossreactivity. The fusion protein RibN-alphaN was therefore constructed and compared with a fusion protein of similar size derived from the repeats, Rib2R-alpha2R. In the rabbit, the fusion protein RibN-alphaN elicited better antibody responses than Rib2R-alpha2R, as judged by reactivity with Rib- or alpha-expressing bacteria (FIG. 3B). For comparisons in the mouse model of passive protection, anti-(RibN-alphaN) was therefore diluted to the same titer as anti-(Rib2R-alpha2R). Each antiserum protected against a Rib-expressing type III strain and an alpha-expressing type Ia strain (FIG. 3 C). Thus, each of the two fusion proteins elicited protective antibodies directed against Rib and alpha.

Example 6

Passive Vaccination for Multiple Serotypes of GBS

The passive vaccination model was used to analyze whether protection provided by anti-(RibN-alphaN) is independent of capsular serotype. Good protection was observed in experiments with a Rib-expressing type II strain and an alpha-expressing type Ib strain (FIG. 3 D). Thus, anti-(RibN-alphaN) protected against Rib- and alpha-expressing strains of the four classical serotypes, Ia, Ib, II and III. This protection was not unspecific, because anti-(RibN-alphaN) did not protect against a Rib-negative mutant (FIG. 3 E). Of note, the Rib negative mutant could be used for this analysis, because it did not show reduced virulence in the mouse model. Antibodies to RibN-alphaN also recognized strains expressing two proteins related to Rib and alpha, the R28 and epsilon proteins, which are expressed by many strains of serotypes V and Ia, respectively (Lindahl et al *Clin. Microbiol. Rev* 2005. 18:102-127; Brimil et al. *Int J. Med. Microbiol.* 2006. 296: 39-44). However, Pprotection against strains expressing R28 or epsilon may require construction of a fusion protein including the N-terminal regions of these proteins.

Example 7

Active Vaccination

Figure 4:
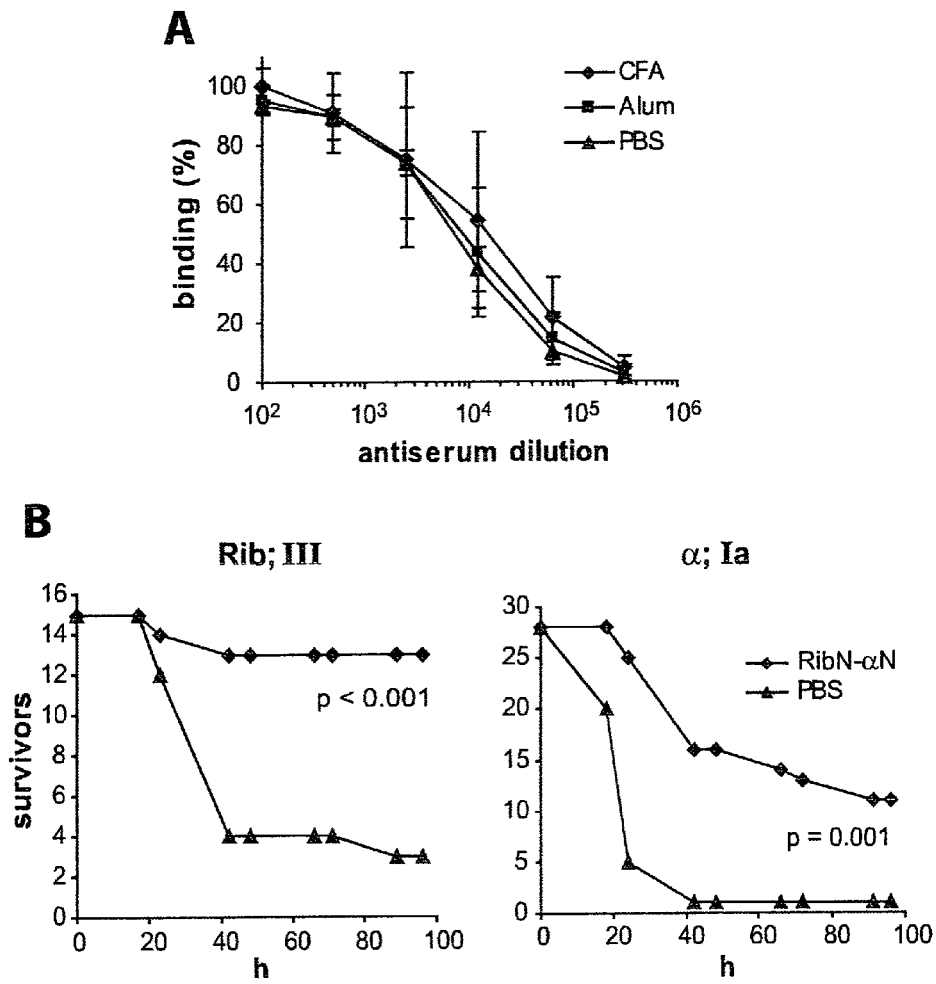
FIG. 4 shows results from active immunization with the RibN-alphaN fusion protein. (A) Immunogenicity of RibN-alphaN when administered with or without adjuvant. (B) Active vaccination with RibN-alphaN.

FIG. 4 shows results from active immunization with the RibN-alphaN fusion protein. (A) Immunogenicity of RibN-alphaN when administered with or without adjuvant. Groups of four mice were immunized with RibN-alphaN mixed with CFA, alum or PBS, boosted after 4 wk and bled 2 wk later. The mouse sera were analyzed for reactivity with the pure antigen immobilized in microtiter wells. Bound mouse antibodies were detected by incubation with rabbit anti-mouse Ig, followed by radiolabeled protein G. (B) Active vaccination with RibN-alphaN. Mice (number indicated on the y-axis) were immunized with pure RibN-alphaN mixed with alum, boosted after 4 wk and challenged 2 wk later with the Rib-expressing type III strain BM110 (left) or the alpha-expressing type Ia strain A909 (right). Control mice received PBS and alum. The data for the alpha-strain are pooled from two experiments. The p values refer to comparisons at 96 h.

In active immunizations with pure RibN-alphaN, this protein was equally immunogenic for mice when administered with CFA, alum or PBS (FIG. 4 A). Moreover, active immunization with RibN-alphaN and alum protected mice against Rib- and alpha-expressing strains (FIG. 4 B). Thus, RibN-alphaN elicited protective immunity with an adjuvant accepted for human use.

The antibodies elicited by RibN-alphaN were almost exclusively of the IgG class (data not shown). Extrapolated to humans, these data suggest that a fetus may be protected by maternal anti-(RibN-alphaN) antibodies. This conclusion is supported by the finding that antibodies to intact Rib and alpha are transferred over the human placenta.

In contrast to the results obtained with RibN-alphaN, the Rib2R-alpha2R protein elicited antibodies in only one of four CFA mice and no antibodies in mice that received antigen with alum or PBS (data not shown). Thus, Rib2R-alpha2R was poorly immunogenic for mice, although intact Rib and alpha elicited good immune responses to the repeats. These data corroborate the conclusion that RibN-alphaN is of particular interest as a vaccine component.

Example 8

Antibodies to RibN-alphaN Prevent Invasion of Epithelial Cells

Figure 5:
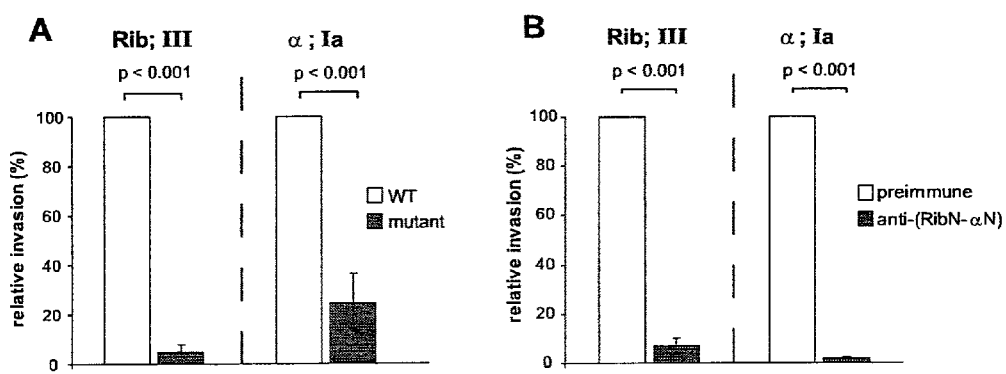
FIG. 5 shows comparison of bacteria for (A) ability to invade cells of the human cervical cell line ME180. (B) Inhibition of epithelial cell invasion by anti-(RibN-alphaN).

FIG. 5 shows that antibodies to RibN-alphaN prevent invasion of human epithelial cells. (A) Role of Rib and alpha in epithelial cell invasion. A Rib-negative mutant of strain BM110 (left) and an alpha-negative mutant of strain A909 (right) were compared with the corresponding wild-type (WT) bacteria for ability to invade cells of the human cervical cell line ME180. (B) Inhibition of epithelial cell invasion by anti-(RibN-alphaN). Bacteria of strain BM110 (left) or A909 (right) were preincubated with rabbit anti-(RibN-alphaN) or with pre-immune serum before use in the invasion assay. All data in panels (A) and B are based on three different experiments. SDs and p values are indicated.

An overnight bacterial culture was washed in PBS, resuspended in DME (supplemented with 10 mM Hepes and 4 mM L-glutamine) to $1 \times 10^7$ CFU ml-1 and a sample (500 μl) was added to a monolayer of the human cervical cell line ME180 (ATCC HTB33), grown to 100% confluence in a well of a 24 well plate. Bacteria added ranged between $6.7 \times 10^6$ CFU and $2.7 \times 10^7$ CFU. The plate was centrifuged at 800×g for 10 min and incubated for 1 h at 37° C. After five washes with PBS, DME (1 ml) containing gentamicin (500 μg ml-1) and penicillin G (5 μg ml-1), was added to each well and incubation was continued for 2 h. After 3 washes with PBS, the cells were detached with trypsin-EDTA and lysed with 0.025% Triton X-100, and intracellular bacteria were determined by plating. To analyze inhibition of invasion by antiserum, washed bacteria (500 μl) were mixed with antiserum (50 μl) and incubated at room temperature for 30 min. The mixture was added to a monolayer of ME180. The number of CFU before and after incubation with antiserum was determined. The analysis was then performed as described above. Pre-immune rabbit serum was used as control. The fraction of bacteria invading ME 180 in the absence of antiserum was 0.13-0.37% of the inoculum.

Studies in a primate model have indicated that GBS invades epithelial cells during an infection. Because alpha promotes invasion of GBS in vitro, we compared the role of Rib and alpha in invasion, using GBS mutants (FIG. 5 A). Invasion of human ME 180 cells was reduced 20-fold for the Rib mutant and 4-fold for the alpha mutant, as compared to the parental strains. Thus, Rib and alpha share ability to promote invasion. This potentially important function was efficiently blocked by anti-(RibN-alphaN) (FIG. 5 B). The reduction in invasion was not due to antibody-mediated bacterial clumping, which did not occur under the conditions used (data not shown). This result suggests that anti-(RibN-alphaN) blocks a biologically important function.

Statistical analysis. Data from mouse protection tests were analyzed with Fisher's 2-tailed exact test. Analysis of data from epithelial cell invasion tests were based on the standard normal approximation of maximum likelihood estimates for two independent binomially distributed variables. Differences were considered statistically significant with $p<0.05$.

In summary, our work shows that the N-terminal regions of Rib and alpha can be used to derive a fusion protein vaccine that is superior to one derived from the repeats. Further, with regard to human GBS vaccines, our data indicate that the RibN-alphaN fusion protein may elicit protective immunity against many clinically important strains, including most strains causing meningitis.

While the preferred embodiment of the present invention has been described in detail by the examples, it is apparent that modifications and adaptations of the present invention will occur to those skilled in the art. It is to be expressly understood, however, that such modifications and adaptations are within the scope of the present invention, as set forth by the claims.

The invention claimed is:

1. A fusion protein comprising at least two amino acid sequences, wherein said two amino acid sequences consists of a first amino acid sequence having at least 90% sequence identity with the amino acid sequence as shown in SEQ ID NO:2, fused to a second amino acid sequence having at least 90% sequence identity with the amino acid sequence as shown in SEQ ID NO:4.

2. The fusion protein according to claim 1, wherein said first amino acid sequence have at least 95, 96, 97, 98 or 99% sequence identity with the amino acid sequence as shown in SEQ ID NO:2 or wherein said second amino acid sequence have at least 95, 96, 97, 98 or 99% sequence identity with the amino acid sequence as shown in SEQ ID NO:4.

3. The fusion protein according to claim 1, wherein the fusion protein comprises an amino acid sequence having at least 90% identity to the amino acid sequence shown in SEQ ID NO:6.

4. The fusion protein according to claim 3, wherein the fusion protein comprises an amino acid sequence having at least 95% identity to the amino acid sequence shown in SEQ ID NO:6.

5. The fusion protein according to claim 1, wherein said fusion protein comprises three or more of the two amino acid sequences.

6. The fusion protein according to claim 1, wherein said fusion protein is modified by glycosylation, amidation, carboxylation or phosphorylation.

7. A vaccine comprising a pharmaceutically effective amount of a fusion protein according to claim 1, wherein said vaccine composition is capable of eliciting protective immunity against group B *Streptococcus* comprising a pharmaceutically acceptable vehicle.

8. The vaccine according to claim 7, which further comprises an adjuvant.

9. The vaccine according to claim 7, wherein said fusion protein is conjugated to a polysaccharide to form a conjugate vaccine.

10. The vaccine according to claim 7, wherein the fusion protein is conjugated to a bacterial polysaccharide.

11. The vaccine according to claim 10, wherein said bacterial polysaccharide is a B *Streptococcus* polysaccharide.

* * * * *

SEQUENCE LISTING

```
<160> NUMBER OF SEQ ID NOS: 6

<210> SEQ ID NO 1
<211> LENGTH: 537
<212> TYPE: DNA
<213> ORGANISM: Streptococcus sp.

<400> SEQUENCE: 1
gggcccctgg gatccgctga agtaatttca ggaagtgctg ttacgttaaa cacaaatatg      60
actaaaaatg ttcagaatgg tagagcatat atagatttat atgatgtgaa aaatgggaaa     120
atagatccat tacaattaat tacgttaaat tcacctgatt taaaagctca gtatgtcatt     180
aggcaaggcg gcaattattt cacacaacct tctgaattga ctactgttgg tgcagctagt     240
attaattata cagtattgaa gacagatgga agtcctcata cgaagcctga tggacaagtg     300
gatattataa acgtttcatt gactatttac aattcttcag ctttgagaga taaaatagat     360
gaagttaaaa agaaagcgga agaccctaaa tgggacgagg gaagtcgcga taaagttttg     420
ataagtttag atgatatcaa aacagatatt gataataatc ctaagacgca atcagacatt     480
gccaataaaa taactgaagt tactaattta gaaaaaatac tagtacctcg aatccca       537

<210> SEQ ID NO 2
<211> LENGTH: 179
<212> TYPE: PRT
<213> ORGANISM: Streptococcus sp.

<400> SEQUENCE: 2
```

```
Gly Pro Leu Gly Ser Ala Glu Val Ile Ser Ser Ala Val Thr Leu
1               5                   10                  15

Asn Thr Asn Met Thr Lys Asn Val Gln Asn Gly Arg Ala Tyr Ile Asp
            20                  25                  30

Leu Tyr Asp Val Lys Asn Gly Lys Ile Asp Pro Leu Gln Leu Ile Thr
        35                  40                  45

Leu Asn Ser Pro Asp Leu Lys Ala Gln Tyr Val Ile Arg Gln Gly Gly
    50                  55                  60

Asn Tyr Phe Thr Gln Pro Ser Glu Leu Thr Thr Val Gly Ala Ala Ser
65                  70                  75                  80

Ile Asn Tyr Thr Val Leu Lys Thr Asp Gly Ser Pro His Thr Lys Pro
                85                  90                  95

Asp Gly Gln Val Asp Ile Ile Asn Val Ser Leu Thr Ile Tyr Asn Ser
            100                 105                 110

Ser Ala Leu Arg Asp Lys Ile Asp Glu Val Lys Lys Ala Glu Asp
        115                 120                 125

Pro Lys Trp Asp Glu Gly Ser Arg Asp Lys Val Leu Ile Ser Leu Asp
        130                 135                 140

Asp Ile Lys Thr Asp Ile Asp Asn Asn Pro Lys Thr Gln Ser Asp Ile
145                 150                 155                 160

Ala Asn Lys Ile Thr Glu Val Thr Asn Leu Glu Lys Ile Leu Val Pro
                165                 170                 175

Arg Ile Pro

<210> SEQ ID NO 3
<211> LENGTH: 525
<212> TYPE: DNA
<213> ORGANISM: Streptococcus sp.

<400> SEQUENCE: 3
gggcccctgg gatcctctac aattccaggg agtgcagcga ccttaaatac aagcatcact    60
aaaaatatac aaaacggaaa tgcttacata gatttatatg atgtaaaatt aggtaaaata   120
gatccattac aattaattgt tttagaacaa ggttttacag caaagtatgt ttttagacaa   180
ggtactaaat actatgggga tgtttctcag ttgcagagta caggaagggc tagtcttacc   240
tataatatat ttggtgaaga tggactacca catgtaaaga ctgatggaca aattgatata   300
gttagtgttg ctttaactat ttatgattca acaaccttga gggataagat tgaagaagtt   360
agaacgaatg caaacgatcc taagtggacg gaagaaagtc gtactgaggt tttaacagga   420
ttagatacaa ttaagacaga tattgataat aatcctaaga cgcaaacaga tattgatagt   480
aaaattgttg aggttaatga attagagaaa ttgttagtat tgtca              525

<210> SEQ ID NO 4
<211> LENGTH: 175
<212> TYPE: PRT
<213> ORGANISM: Streptococcus sp.

<400> SEQUENCE: 4

Gly Pro Leu Gly Ser Ser Thr Ile Pro Gly Ser Ala Ala Thr Leu Asn
1               5                   10                  15

Thr Ser Ile Thr Lys Asn Ile Gln Asn Gly Asn Ala Tyr Ile Asp Leu
            20                  25                  30

Tyr Asp Val Lys Leu Gly Lys Ile Asp Pro Leu Gln Leu Ile Val Leu
        35                  40                  45

Glu Gln Gly Phe Thr Ala Lys Tyr Val Phe Arg Gln Gly Thr Lys Tyr
    50                  55                  60
```

Tyr Gly Asp Val Ser Gln Leu Gln Ser Thr Gly Arg Ala Ser Leu Thr
65                  70                  75                  80

Tyr Asn Ile Phe Gly Glu Asp Gly Leu Pro His Val Lys Thr Asp Gly
                85                  90                  95

Gln Ile Asp Ile Val Ser Val Ala Leu Thr Ile Tyr Asp Ser Thr Thr
            100                 105                 110

Leu Arg Asp Lys Ile Glu Glu Val Arg Thr Asn Ala Asn Asp Pro Lys
        115                 120                 125

Trp Thr Glu Glu Ser Arg Thr Glu Val Leu Thr Gly Leu Asp Thr Ile
    130                 135                 140

Lys Thr Asp Ile Asp Asn Asn Pro Lys Thr Gln Thr Asp Ile Asp Ser
145                 150                 155                 160

Lys Ile Val Glu Val Asn Glu Leu Glu Lys Leu Leu Val Leu Ser
                165                 170                 175

<210> SEQ ID NO 5
<211> LENGTH: 1053
<212> TYPE: DNA
<213> ORGANISM: Streptococcus sp.

<400> SEQUENCE: 5
gggcccctgg gatccgctga agtaatttca ggaagtgctg ttacgttaaa cacaaatatg    60
actaaaaatg ttcagaatgg tagagcatat atagatttat atgatgtgaa aaatgggaaa   120
atagatccat acaattaat tacgttaaat tcacctgatt taaaagctca gtatgtcatt    180
aggcaaggcg gcaattattt cacacaacct tctgaattga ctactgttgg tgcagctagt   240
attaattata cagtattgaa gacagatgga agtcctcata cgaagcctga tggacaagtg   300
gatattataa acgtttcatt gactatttac aattcttcag ctttgagaga taaaatagat   360
gaagttaaaa agaaagcgga agaccctaaa tgggacgagg gaagtcgcga taagttttg   420
ataagtttag atgatatcaa aacagatatt gataataatc ctaagacgca atcagacatt   480
gccaataaaa taactgaagt tactaattta gaaaaaatac tagtacctcg aatcccagaa   540
ttctctacaa ttccagggag tgcagcgacc ttaaatacaa gcatcactaa aaatatacaa   600
aacggaaatg cttacataga tttatatgat gtaaaattag gtaaaataga tccattacaa   660
ttaattgttt tagaacaagg ttttacagca aagtatgttt ttagacaagg tactaaatac   720
tatggggatg tttctcagtt gcagagtaca ggaagggcta gtcttaccta taatatattt   780
ggtgaagatg gactaccaca tgtaaagact gatggacaaa ttgatatagt tagtgttgct   840
ttaactattt atgattcaac aaccttgagg gataagattg aagaagttag aacgaatgca   900
aacgatccta gtggacggaa agaaagtcgt actgaggttt taacaggatt agatacaatt   960
aagacagata ttgataataa tcctaagacg caaacagata ttgatagtaa aattgttgag  1020
gttaatgaat tagagaaatt gttagtattg tca                                1053

<210> SEQ ID NO 6
<211> LENGTH: 378
<212> TYPE: PRT
<213> ORGANISM: Streptococcus sp.

<400> SEQUENCE: 6

Gly Pro Leu Gly Ser Ala Ser Val Leu Ile Gly Ile Ser Phe Leu Gly
1               5                   10                  15

Gly Phe Thr Gln Gly Gln Phe Asn Ile Ser Thr Asp Thr Val Phe Ala
            20                  25                  30

-continued

```
Ala Glu Val Ile Ser Gly Ser Ala Val Thr Leu Asn Thr Asn Met Thr
    35                  40                  45
Lys Asn Val Gln Asn Gly Arg Ala Tyr Ile Asp Leu Tyr Asp Val Lys
50                  55                  60
Asn Gly Lys Ile Asp Pro Leu Gln Leu Ile Thr Leu Asn Ser Pro Asp
65                  70                  75                  80
Leu Lys Ala Gln Tyr Val Ile Arg Gln Gly Gly Asn Tyr Phe Thr Gln
                85                  90                  95
Pro Ser Glu Leu Thr Thr Val Gly Ala Ala Ser Ile Asn Tyr Thr Val
            100                 105                 110
Leu Lys Thr Asp Gly Ser Pro His Thr Lys Pro Asp Gly Gln Val Asp
        115                 120                 125
Ile Ile Asn Val Ser Leu Thr Ile Tyr Asn Ser Ser Ala Leu Arg Asp
    130                 135                 140
Lys Ile Asp Glu Val Lys Lys Ala Glu Asp Pro Lys Trp Asp Glu
145                 150                 155                 160
Gly Ser Arg Asp Lys Val Leu Ile Ser Leu Asp Asp Ile Lys Thr Asp
                165                 170                 175
Ile Asp Asn Asn Pro Lys Thr Gln Ser Asp Ile Ala Asn Lys Ile Thr
            180                 185                 190
Glu Val Thr Asn Leu Glu Lys Ile Leu Val Pro Arg Ile Pro Glu Phe
        195                 200                 205
Ser Thr Ile Pro Gly Ser Ala Ala Thr Leu Asn Thr Ser Ile Thr Lys
    210                 215                 220
Asn Ile Gln Asn Gly Asn Ala Tyr Ile Asp Leu Tyr Asp Val Lys Leu
225                 230                 235                 240
Gly Lys Ile Asp Pro Leu Gln Leu Ile Val Leu Glu Gln Gly Phe Thr
                245                 250                 255
Ala Lys Tyr Val Phe Arg Gln Gly Thr Lys Tyr Tyr Gly Asp Val Ser
            260                 265                 270
Gln Leu Gln Ser Thr Gly Arg Ala Ser Leu Thr Tyr Asn Ile Phe Gly
        275                 280                 285
Glu Asp Gly Leu Pro His Val Lys Thr Asp Gly Gln Ile Asp Ile Val
    290                 295                 300
Ser Val Ala Leu Thr Ile Tyr Asp Ser Thr Thr Leu Arg Asp Lys Ile
305                 310                 315                 320
Glu Glu Val Arg Thr Asn Ala Asn Asp Pro Lys Trp Thr Glu Glu Ser
                325                 330                 335
Arg Thr Glu Val Leu Thr Gly Leu Asp Thr Ile Lys Thr Asp Ile Asp
            340                 345                 350
Asn Asn Pro Lys Thr Gln Thr Asp Ile Asp Ser Lys Ile Val Glu Val
        355                 360                 365
Asn Glu Leu Glu Lys Leu Leu Val Leu Ser
    370                 375
```